United States Patent

Nyqvist-Mayer et al.

[11] Patent Number: 5,773,022
[45] Date of Patent: Jun. 30, 1998

[54] TOPICAL DRESSING

[75] Inventors: Adela Nyqvist-Mayer, Tullinge, Sweden; Peter Walter, Ortenberg, Germany

[73] Assignee: Astra AB, Sweden

[21] Appl. No.: 532,687

[22] PCT Filed: Apr. 5, 1995

[86] PCT No.: PCT/SE95/00368

§ 371 Date: Aug. 22, 1996

§ 102(e) Date: Aug. 22, 1996

[87] PCT Pub. No.: WO95/26778

PCT Pub. Date: Oct. 12, 1995

[30] Foreign Application Priority Data

Apr. 5, 1994 [SE] Sweden .................................. 9401133
Sep. 19, 1994 [SE] Sweden .................................. 9403122

[51] Int. Cl.⁶ ............................. A61F 13/02; A61K 9/70; A61L 15/16
[52] U.S. Cl. .......................... 424/443; 424/448; 424/449
[58] Field of Search .................................. 424/443, 448, 424/449; 604/304, 307, 19, 93

[56] References Cited

U.S. PATENT DOCUMENTS

| D. 377,529 | 1/1997 | Nyqvist-Mayer | D24/189 |
| 3,900,027 | 8/1975 | Keedwell | 128/268 |
| 4,695,277 | 9/1987 | Lauk | 604/304 |
| 4,849,224 | 7/1989 | Chang et al. | 424/434 |
| 4,915,102 | 4/1990 | Kwiatek et al. | 128/156 |
| 5,268,179 | 12/1993 | Rudella | 424/449 |

FOREIGN PATENT DOCUMENTS

| B-75975/91 | 11/1992 | Australia | A61M 37/00 |
| 3204582 | 8/1983 | Germany | A61F 13/02 |
| 163438 | 2/1986 | Norway | A61F 13/02 |
| WO85/00287 | 1/1985 | WIPO | A61F 13/02 |

OTHER PUBLICATIONS

Dialog abstract of German patent document DE 3204582 (listed above as document AM1), Derwent World Patents Index accession No. 83–747746/35.

Dialog abstract of Norwegian patent document NO 163438 (listed above as document AN1), Derwent World Patents Index accession No. 86–049686/08.

Primary Examiner—Gollamudi S. Kishore
Assistant Examiner—Kathryne E. Shelborne
Attorney, Agent, or Firm—Michael A. Sanzo; Vinson & Elkins

[57] ABSTRACT

A topical dressing for dermal or transdermal administration of a substance, comprising a backing structure comprising a disc, a pad containing the active substance, a resilient layer with an adhesive provided on one side thereof, the resilient layer and the adhesive being provided with a cut-out defining a cavity in which the pad is placed, the disc of the backing structure being provided on the side of the resilient layer remote from the side provided with the adhesive and partly covering the resilient layer, and a covering structure having a release layer and a dish, the dish being formed to receive the pad during production and storage of the dressing, said covering structure being provided on the adhesive side of the resilient layer, whereby the backing structure is provided with one or more strips extending outwardly from the periphery edge of the backing disc towards the periphery edges of the resilient layer and in that the cover structure and the backing structure are sealed together within the cavity. There is also provided a method of producing a topical dressing according to the invention.

13 Claims, 2 Drawing Sheets

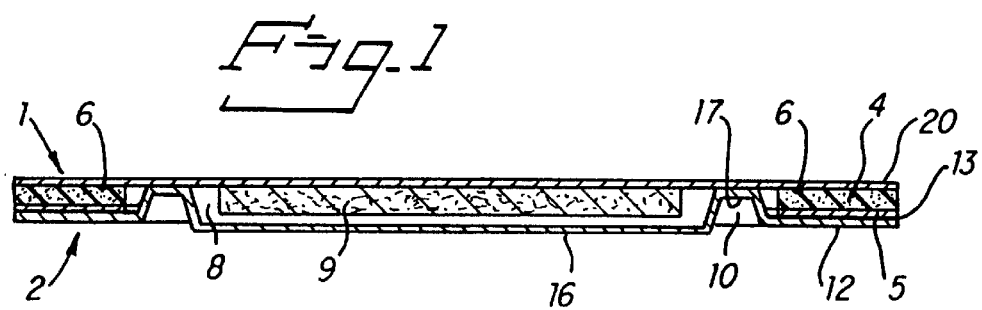
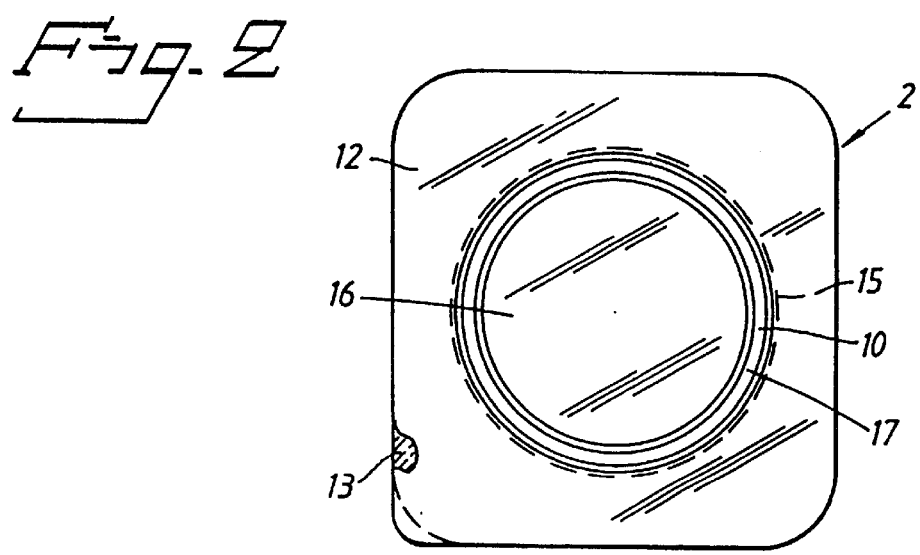
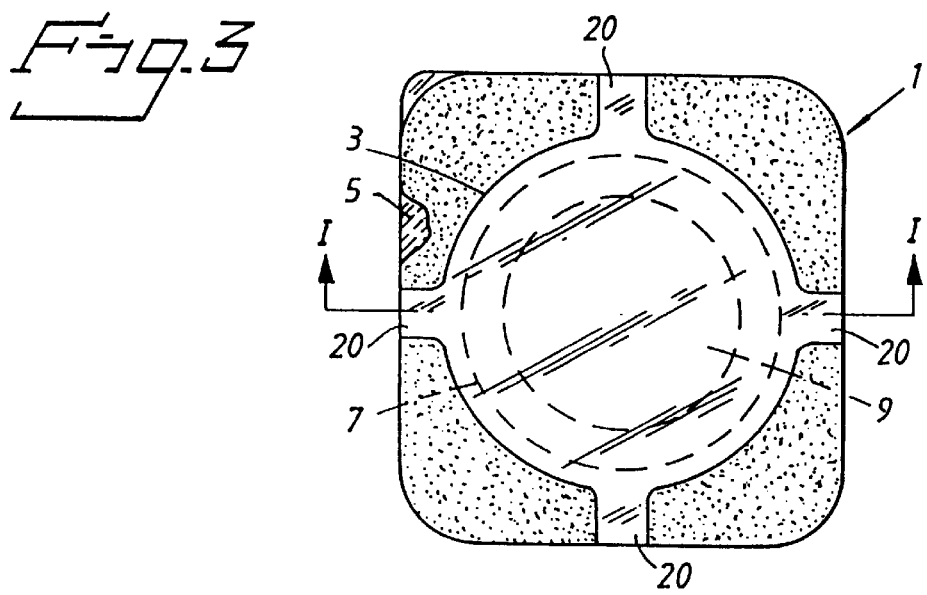

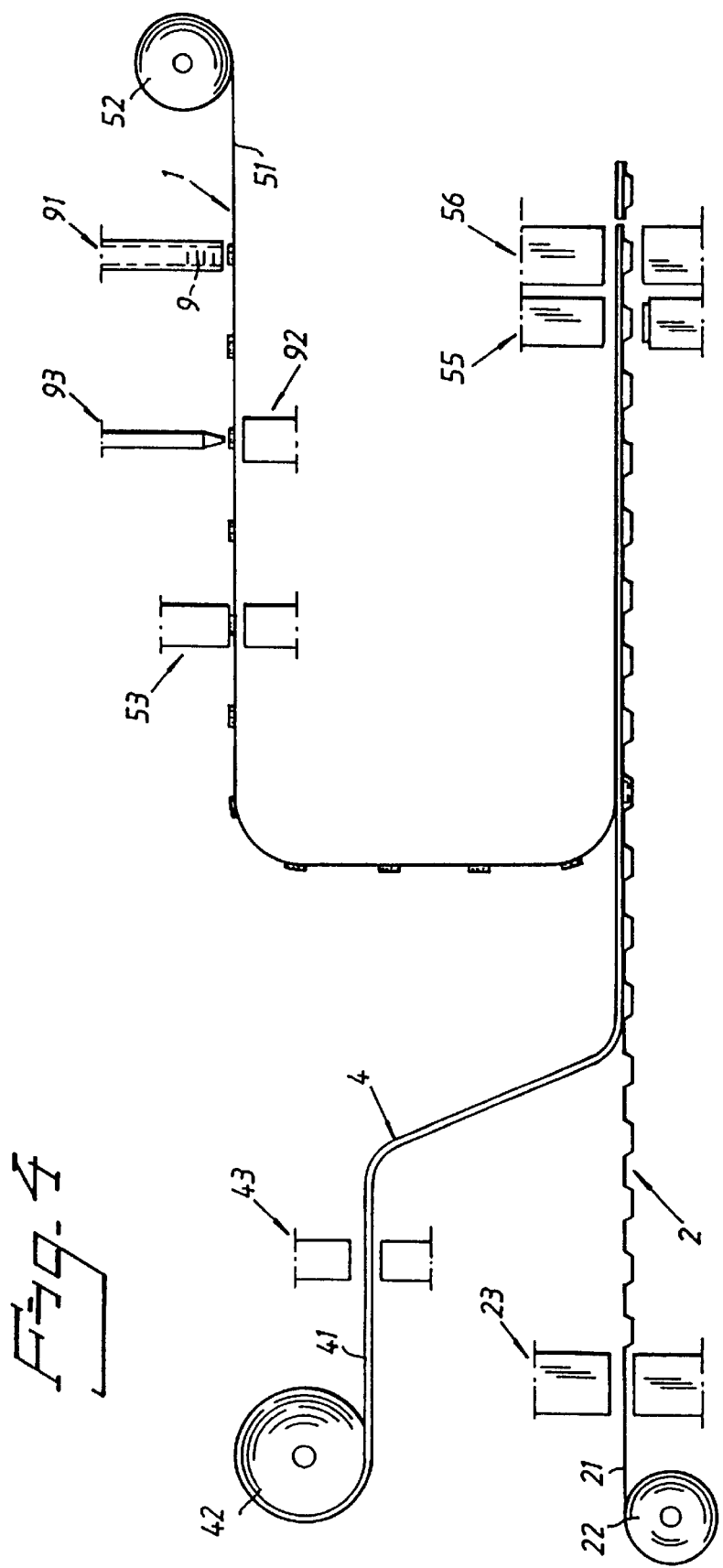

TOPICAL DRESSING

FIELD OF THE INVENTION

The invention is related to a topical dressing for dermal or transdermal administration of a substance, comprising the features of the preamble of claim 1.

The invention is also related to a method of manufacturing the topical dressing for dermal or transdermal administration according to the invention.

BACKGROUND OF THE INVENTION

This invention relates to dressings for use in the topical administration of drugs and other substances.

It is known to administer drugs dermally and transdermally i.e. by maintaining a drug in intimate contact with a patients skin so that the active constituent slowly passes into and through the skin and is absorbed into the patient's body over a prolonged period of time.

The drug is usually held in position for the requisite period of time using an adhesive patch.

EP-A-0013606 describes an adhesive patch for transdermal drug administration which comprises a laminated backing strip shaped to provide a cavity which is filled with a polymeric matrix containing the drug to be administered. The cavity is bounded with skin adhesive and is sealed by a laminated cover strip which is held in position by the adhesive. The cover strip is provided with a surface layer of release material so that it can be readily separated from the backing strip to expose the polymeric diffusion matrix and the skin adhesive for use.

EP-B-0181333 describes an adhesive patch for transdermal administration which comprises a backing strip having a ring of microporous material fixed to a support sheet which is a polyethylene/metal foil/polyester laminate. The ring of microporous material has a surface layer of skin adhesive and defines a central cavity which contains the drug to be administered. A cover strip is formed from the same laminated material as the above mentioned support sheet and is held in position to seal the cavity by engagement of a release layer on the surface of the cover strip with the skin adhesive, and by means of a heat seal ring between the laminated materials of the backing strip and the cover strip beyond the outer periphery of the ring of microporous material. The drug in the cavity and the skin adhesive are exposed for use by separating a portion of the lamination material of the backing strip with the attached ring of microporous material by tearing the laminated material around a ring of perforations.

With the above mentioned known constructions sealing of the cavity is achieved by virtue of the engagement between the layer skin adhesive on the backing strip and the release layer on the cover strip, and in the case of EP-B-0181333 also by means of the outer heat seal ring. With this arrangement there is the problem that the drug in the cavity may at least partially escape, e.g. by diffusion into the surrounding adhesive and/or other layers, especially if the drug is of a mobile or volatile nature, and particularly if the drug is present in the cavity by itself or absorbed on a pad or otherwise in readily releasable form rather than being incorporated in a rotentive medium such as the polymeric matrix of EP-A-0013606. Since transdermal dressings may be used for accurate administration of predetermined quantities of drugs it will be appreciated that escape of quantities of the drug from the cavity can constitute a serious problem.

A topical dressing of the above mentioned type is also described in Australian Patent Application No. 75975/91. This dressing is provided with a backing layer which contains a backing sheet which only partly covers the resilient layer.

In the above mentioned Australian dokument the backing sheet is provided as single pieces of backing which, during production, are intended to be placed, one by one, on the continuous layer of resilient material at predetermined positions. This is a procedure which however gives raise to a new problem. Because the backing sheet is made of a very thin material, about 10–50μm, the edges of the pieces of backing will bend upwards which makes the application of the discs on the resilient structure more difficult and, under certain circumstances, almost impossible. Even if the disc is placed properly on to the resilient structure the sealing between the disc and the resilient structure might be negatively influenced and leakage could occur during use of the patch.

The most obvious way to solve this problem is to provide the backing disc or sheet as a continuous layer covering the whole continuous layer of resilient material. This will however provide a non-flexible dressing which would be difficult to apply on several parts of the body such as elbows, knees, hands etc. It would also create a significant discomfort for the user. Therefore the backing sheet has to be smaller than the resilient material in the final patch.

It is therefore necessary to solve this problem without deteriorate the flexibility of the final product.

THE INVENTION

It is therefore an object of the present invention to provide a topical dressing of the above mentioned type which overcomes the drawbacks with the known dressings and which provides a dressing which adheres properly to the skin of the user without leakage of the active substance and which is easy to apply and comfortable for the user when dispatched on the skin. It is also simple and convenient to manufacture and which can be readily unsealed when required for application to the skin.

In its first aspect, the invention is directed to a topical dressing comprising a backing structure and a covering structure. The backing structure comprises a pad containing active substance, a resilient layer and a disc. Adhesive is provided on one side of the resilient layer which contains a cut-out region defining a cavity in which the pad is placed. The disc is provided on the side of the resilient layer remote from the side with adhesive and has one or more reinforcement strips extending outward from the peripheral edge of the disc toward the peripheral edge of the resilient layer.

The covering structure is provided on the side of the resilient layer containing adhesive and is sealed to the backing structure within the cavity. The covering structure comprises a release liner and a dish formed to receive the pad during the production and storage of the topical dressing.

In a preferred embodiment, the disc of the topical dressing is provided with four reinforcement strips at about a 90° angle with respect to one another. Both the disc and reinforcement strips may be made by a process comprising cutting parts out of a continuous elongate sheet.

In another preferred embodiment, the covering structure of the topical dressing comprises a covering disc having a ridge and a release liner in which the ridge overlays the cavity of the topical dressing containing the pad. The ridge is held in contact with the backing disc between the pad and the surrounding resilient layer, thereby defining a seal around the pad.

In another aspect, the present invention is directed to a method of manufacturing a topical dressing. This is accomplished by supplying a first continuous elongate sheet of impermeable material and stamping out ridges in this sheet. A continuous elongate resilient layer is also provided by supplying a continuous sheet of resilient material; forming cut-outs in the resilient material; applying a adhesive to one side; and then applying a release liner to the adhesive. The continuous elongate resilient layer is applied to the first continuous elongate sheet in such a manner that the side of resilient material with adhesive and release liner is brought into contact with the continuous elongate sheet. The cut-outs and release liner of the resilient material and the ridges of the first continuous elongate sheet are aligned in a superimposed relationship so as to define cavities.

In the next step of the process, a continuous elongate backing sheet is provided by: supplying a second continuous elongate sheet of impermeable material; applying pads of porous material to the second continuous elongate sheet; and cutting away part of the impermeable material to form the second continuous elongate sheet into discs in which one or more strips extend outward from the periphery of the discs. A continuous sheet of dressing is then formed by placing the continuous elongate backing sheet with pads on top of the continuous elongate resilient layer so as to cover the cavities and partly cover the resilient layer. The pads of the continuous elongate backing sheet are positioned within the ridges of the first continuous elongate sheet. Finally, the continuous sheet of dressing is cut to provide a single topical dressing.

In a preferred embodiment, the second continuous elongate sheet is cut into discs that are substantially circular or oval, with strips extending outward from their periphery. The material which is not part of the end product may be removed from the continuous elongate resilient layer so that the reinforcement strips connect the discs to one another. Preferably, four strips will be formed for each disc and arranged along the periphery of the disc at an angle of about 90° with respect to one another. In one embodiment, the active substance to be supplied by the topical dressing is applied to the pads before they are attached to the continuous elongate backing sheet. In an alternative embodiment, the active substance is applied to the pads after the pads are attached to the backing sheet.

In another aspect, the invention is directed to a method for dermally or transdermally administering an active substance to a subject by applying the topical dressings described above to the subject's skin. Preferably, the active substance is a local anesthetic such as EMLA®(lidocaine/prilocaine)

BRIEF DESCRIPTION OF THE DRAWINGS

The topical dressing according to the present invention will now be described by way of example with reference to the appended drawings, wherein FIG. 1 is a sectional view of the preferred embodiment of the dressing according to the invention, taken along lines I—I in FIG. 3, FIG. 2 is a face view of the of cover structure of the dressing in FIG. 1, FIG. 3 is a face view of the of backing structure of the dressing in FIG. 1, FIG. 4 is a diagrammatic illustration of a method of manufacturing the dressing.

DETAILED DESCRIPTION OF THE DRAWINGS

The dressing is now described in relation to a preferred embodiment of the dressing according to the invention.

The dressing has a backing structure 1 and a cover structure 2, as can be seen in FIG. 1 to 3.

The backing structure 1 comprises a disc 3 which is preferably, but not necessarily, circular and made of impermeable material, e.g. a laminate such as for example a metal foil coated on opposite sides with polymer layers. One side of the laminate or one of the polymer layers is fixed centrally to a layer 4 of resilient material, such as for example plastic foam material. The resilient foam material is coated with a layer 5 of an adhesive which adheres to the skin of a user.

The covering structure is made of an impermeable material, e.g. a laminate such as for example a metal foil coated on one side with a polymer layer. In the preferred embodiment of the invention the covering structure is made of a metal foil which is thicker and more rigid than the material of the backing structure.

This covering structure provides a support for the dressing in order to prevent deformation of the dressing and leakage of the active substance during storage and handling.

In order to prevent the bending up of the edges of the disc 3, when it is placed on the resilient layer during the manufacture process, the disc 3 is provided with reinforcing strips 20. These strips 20 are preferably, but not necessarily, four and extending from the periphery edge of the disc 3 outwardly to the periphery edges of the resilient layer 4 and provided along the periphery of the disc 3 in preferably, but not necessarily, about 90° relation to each other, see FIG. 3. The strips 20 are of the same material as the disc 3 and fixed to the resilient layer 4. The size of the strips 20 is determined by the distance between the periphery edge of the disc 3 and the periphery edges of the resilient material 4. Tests have shown that best result, that is a total elimination of the "bending up-effect" is achieved when the strips 20 are positioned centrally along the sides of the resilient layer 4 as can be seen in FIG. 2. The strips 20 must have a certain sideward extension, eg. a certain breadth, for the wanted effect to be achieved but it must be as small as possible in order to not significantly deteriorate the resiliency of the resilient layer 4. In the preferred embodiment the breadth of the strips 20 is about 5to 20, preferably about 10%, of the total length of the sides of the resilient layer.

The disc 3 is centrally fixed to the resilient layer 4. The resilient layer 4 has a centrally provided substantially circular cut-out 7. The entire surface of the resilient layer is coated with the adhesive 5 and the centrally provided cut-out is totally free from such adhesive.

A cavity 8 is defined within the cut-out 7 and a disc-shaped pad 9 of a porous material is placed within the cavity 8. The thickness of the pad 9 is slightly thicker than the thickness of the resilient layer 4. The pad is located centrally in the cavity and has a diameter which is smaller than the diameter of the cut-out 7 so that an annular space 10 is defined therebetween. The pad is fixed to the disc 3 in any suitable manner such as for example heat sealing.

The cover structure 2 comprises a disc 12 of impermeable material such as a metal foil coated on both sides with polymer layers. One side of the disc 12 is fixed to a sheet of a release liner 13 and the disc 12 could be fixed to the release liner 13 by a circular heat seal. The release liner 13 is provided with a central cut-out 15 having the same size as the cut-out 7 in the resilient layer 4.

The cover structure 2 is applied to the backing structure 1 so that the liner 13 is in aligned superimposed relationship with the adhesive-coated resilient layer 4 and the two structures 1 and 2 are held together by the adhesive 5 and a seal between the discs 3 and 12.

The central circular portion 16 of the disc 12 is formed so that a substantially circular ridge 17 is provided thereby defining a dish 18. The form of the ridge 17 is chosen so that it will be placed within the confines of the cut-out 15 in the release liner 13 and resilient layer 4 when the cover structure 2 and the backing structure 1 are joined together. In this position the ridge 17 will project through the two cut-outs 15 and 7 into engagement with the disc 3. The ridge 17 is heat sealed to the disc 3.

The active substance intended to be dermally and transdermally administered by the use of the dressing according to the invention is absorbed in the pad 9. The pad is made of a porous material, preferably cellulose-material.

Examples of active substances which can be dermally and transdermally administered by using a topical dressing according to the invention are local anaesthetics, such as EMLA®, analgesics, steroids, nicotine, antibiotics.

Due to the preferred construction of the dressing the active substance is wholly sealed between the disc 3 and the disc 12 whereby there is no possibility that the substance could escape into adjacent layers.

When the dressing is to be used the covering structure 2 is peeled off whereby it separates from the adhesive layer 5 at the release liner 13 and the ridge 17 pulls away from the disc 3 rupturing the seal therebetween. The dressing can then be applied to the skin so that the adhesive layer 5 holds the dressing in position with the pad 9 in contact with the skin.

The topical dressing according to the invention can be readily filled and securely closed, and advantageous manufacture can be achieved on a mass production basis whilst ensuring adequate levels of hygiene and security. Moreover, the resulting dressing is particularly convenient to use and effective medication can be achieved whilst avoiding escape of substances likely to contaminate clothing and be uncomfortable for the patient.

The dressing described above can be manufactured by using a method as described below with reference to FIG. 4.

The impermeable laminate of the covering structure is prefabricated and provided as a first continuous elongated sheet 21 on a first roller 22. The ridge 17 is formed in first sheet 21 in a stamping station 23 thereby providing a dish 18.

The resilient layer 4 with the adhesive 5 and the release liner 13 is supplied as a second continuous elongated sheet 41 from a second roller 42 and the cut-outs 7 are provided in a cutting station 43. The cut-outs defines the cavities 8 in the resilient structure. After the cutting this second elongate sheet 41 is placed on top of the laminate of the covering structure, e.g. the first sheet 21 and fixed thereto, preferably by heat sealing.

In a parallel production line the backing structure 1 is manufactured. The impermeable laminate of the backing structure is prefabricated and supplied as a continous elongate sheet 51 and provided on a third roller 52. Thereafter the pads 9 which have been prefabricated are applied from colons 91, placed on the backing sheet and sealed to it in a sealing station 92. The active substance is thereafter applied to the pads 9 at the filling station 93. According to the above it is preferred to apply the active substance pads after they have been placed and sealed to backing sheet but it is also possible to apply the active substance before the step of placing and sealing.

After the filling of the pads the elongate sheet 51 is passed on to a cutting station 53. Here the parts of the material of the laminate which do not form part of the disc 3 and the strips 20 are cut away in such a manner that the backing material is still kept as an elongate sheet whereby strips provided on adjacent discs are connected to each other. Hereby the bend-up of the edges of the discs is avoided which, as described above, facilitates the handling and manufacture significantly.

In the next step the continuous elongate sheet of discs 3 and strips 20, with the pads 9, is turned upside-down and placed on top of the resilient layer 4 as can be seen in FIG. 4. The pads 9 are thereby placed within the dish 18 defined by the ridge 17. Thereafter the resilient layer 4 and the covering 2 on the one hand and the backing disc 3 and the ridge 17 on the other hand are fixed together, preferably by using heat sealing, at a sealing station 55. Circular heat sealing rings 6 are thereby provided surrounding the cavity 8, the ridge 17, the dish 18 with the pad 9 and the cut-outs 7.

The continuous sheet of dressings which is the result of the above described method is cut in a cutting station 56 in order to provide the single pieces of dressings.

Possible Modifications of the Invention

The dressing and the manufacturing method according to the invention could of course be modified within the scope of the appended claims.

Thus, the materials chosen above can be changed as well as the form and sizes of the different parts. In particular the cut-outs and the disc of the backing structure must not necessarily be circular but could have any other suitable form, such as being oval, quadratic or rectangular. The strips 20 could be provided differently around the periphery of the disc of the backing structure and could have different forms. It is however important to avoid the bend-up effect of the edges of the disc during the manufacture of the dressing. The backing structure must be flexible but at the same time provide a impermeable backing support for the active agent.

The backing structure and the covering structure may be formed from the same or different materials, preferably a metal foil/polymer laminate but any other material having similar characteristics may be used. The polymer content of the laminate may be polyethylene, polypropylene, polyester, ionomer.

The working stations as well as the steps of the manufacturing line can also be modified within the scope of the appended claims

We claim:

1. A topical dressing comprising:
   a) a backing structure comprising:
      i) a pad containing active substance;
      ii) a resilient layer wherein:
         adhesive is provided on one side of said resilient layer; and
         said resilient layer is provided with a cut-out region defining a cavity in which said pad is placed; and
      iii) a disc wherein:
         said disc is provided on the side of said resilient layer remote from the side with adhesive;
         said disc is provided with one or more reinforcement strips extending outward from the peripheral edge of said disc toward the peripheral edge of said resilient layer, and
   b) a covering structure, provided on the adhesive side of said resilient layer and sealed to said backing structure within said cavity and wherein said covering structure comprises
      i) a release liner; and ii) a disc formed to receive said pad during production and storage of said topical dressing.

2. The topical dressing of claim 1, wherein said disc is provided with four reinforcement strips at about a 90° angle with respect to one another.

3. The topical dressing of claim 1, wherein said disc and reinforcement strips are made by a process comprising cutting parts out of a continuous elongate sheet.

4. The topical dressing of any one of claims 1–3 wherein said covering structure comprises a covering disc having a ridge and release liner, and wherein:
   a) said ridge overlays said cavity containing said pad; and
   b) said ridge is held in contact with the backing disc between said pad and the surrounding resilient layer, thereby defining a seal around said pad.

5. A method of manufacturing a topical dressing comprising:
   a) supplying a first continuous elongate sheet of impermeable material;
   b) stamping out ridges in said impermeable material in said first continuous elongate sheet;
   c) providing a continuous elongate resilient layer by a process comprising
      i) supplying a continuous sheet of resilient material;
      ii) forming cut-outs in said resilient material;
      iii) applying adhesive to one side of said resilient material;
      iv) applying a release liner to said adhesive;
   d) applying said continuous elongate resilient layer to said first continuous elongate sheet in such a manner that:
      i) the side of said resilient material with adhesive and release liner is placed onto said first continuous elongate sheet;
      ii) the cut-outs and release liner of said resilient material and the ridges of said first continuous elongate sheet are aligned in a superimposed relationship so as to define cavities;
   e) providing a continuous elongate backing sheet by a process comprising:
      i) supplying a second continuous elongate sheet of impermeable material;
      ii) applying pads of porous material to said second continuous elongate sheet;
      iii) cutting away part of said impermeable material to form said second continuous elongate sheet into discs wherein one or more strips extend from the periphery of said discs;
   f) forming a continuous sheet of dressing by placing said continuous elongate backing sheet with pads on top of said continuous elongate resilient layer so as to cover said cavities and partly cover said resilient layer, and wherein said pads are positioned within said ridges; and
   g) cutting said continuous sheet of dressing to provide a single topical dressing.

6. The method of claim 5, wherein said backing sheet is cut into discs that are substantially circular or oval, and wherein strips extend outward from the periphery of said discs.

7. The method of claim 6, wherein the material which is not part of the end product is removed from said continuous elongate resilient layer so that said strips connect said discs to one another.

8. The method of claim 6, wherein four strips are formed for each disc and said strips are arranged along the periphery of said disc at an angle of about 90° with respect to one another.

9. The method of claim 5, wherein active substance is applied to said pads before said pads are applied to said continuous elongate backing sheet.

10. The method of claim 5, wherein active substance is applied to said pads after said pads are applied to said continuous elongate backing sheet.

11. A method for dermally or transdermally administering an active substance to a subject, comprising the step of applying the topical dressing of claim 1 to the skin of said subject.

12. The method of claim 11, wherein said active substance is a local anesthetic.

13. The method of claim 12, wherein said local anesthetic comprises lidocaine and prilocaine.

* * * * *